(12) United States Patent
Lemaire et al.

(10) Patent No.: US 8,912,365 B2
(45) Date of Patent: Dec. 16, 2014

(54) PROCESS FOR PREPARING A POLYOL ETHER

(75) Inventors: Marc Lemaire, Villeurbanne (FR); Wissam Dayoub, Villeurbanne (FR); Marc Sutter, Villeurbanne (FR); Yann Raoul, Crezancy (FR)

(73) Assignees: Fonds de Developpement des Filieres des Oleagineux et Proteagineux Fidop, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/993,980

(22) PCT Filed: Dec. 16, 2011

(86) PCT No.: PCT/FR2011/053039
§ 371 (c)(1),
(2), (4) Date: Oct. 1, 2013

(87) PCT Pub. No.: WO2012/080682
PCT Pub. Date: Jun. 21, 2012

(65) Prior Publication Data
US 2014/0018579 A1    Jan. 16, 2014

(30) Foreign Application Priority Data
Dec. 17, 2010   (FR) ..................................... 10 60745

(51) Int. Cl.
C07C 41/16    (2006.01)
C07C 41/01    (2006.01)
C07C 41/00    (2006.01)

(52) U.S. Cl.
CPC ................. *C07C 41/00* (2013.01); *C07C 41/01* (2013.01)
USPC .......................................... 568/680; 549/347

(58) Field of Classification Search
USPC .......................................... 568/678, 679, 680
See application file for complete search history.

(56) References Cited

U.S. PATENT DOCUMENTS

| | | |
|---|---|---|
| 5,446,210 A | 8/1995 | Hees et al. |
| 6,218,580 B1 | 4/2001 | Morawietz et al. |
| 2006/0128979 A1 | 6/2006 | Choo et al. |
| 2010/0048940 A1* | 2/2010 | Tulchinsky et al. .......... 560/186 |

FOREIGN PATENT DOCUMENTS

| | | |
|---|---|---|
| EP | 0624563 | 11/1994 |
| WO | WO 2010/027663 | 3/2010 |

OTHER PUBLICATIONS

Shi Y et al.: "Straightforward selective synthesis of linear 1-O-alkyl glycerol and di-glycerol monoethers"; Tetrahedron Letters, Elsevier, Amsterdam, NL, vol. 50, No. 49, Dec. 9, 2009, pp. 6891-6893, XP026699729.
Shi et al.: "One-step selective synthesis of branched 1-O-alkyl-glycerol/diglycerol monoethers by catalytic reductive alkylation of ketones"; Science China Chemistry, vol. 53, No. 9, Sep. 1, 2010, pp. 1953-1956, XP002649430.
Avaev et al.: "Effect of the nature of the carrier and reduction conditions on the properties of rhenium catalysts of hydrogenation of ethyl acetate", Russian Chemical Bulletin, vol. 37, No. 1, Jan. 1, 1988, pp. 15-19, XP002649434.
Mao et al.: Catalytic hydrosilation of organic esters using manganese carbonyl acetyl complexes, $(L)(CO)_4MnC(O)CH_3(L=CO, PPh_3)$, Journal of the American Chemical Society, American Chemical Society, Washington, DC.; US, vol. 117, No. 40, Jan. 1, 1995, pp. 10139-10140, XP002270419.

* cited by examiner

*Primary Examiner* — Brian J Davis
(74) *Attorney, Agent, or Firm* — Hamre, Schumann, Mueller & Larson, P.C.

(57) ABSTRACT

The present invention relates to a process for preparing a polyol ether of formula (I), comprising a step of reductive alkylation involving a compound of general formula (II) and a compound of general formula (III):

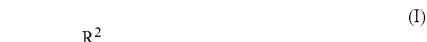

(I)

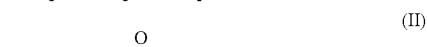

(II)

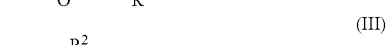

(III)

in which $R^1$, $R^2$, $R^3$ and $R^4$ are as defined in claim 1.

24 Claims, 1 Drawing Sheet

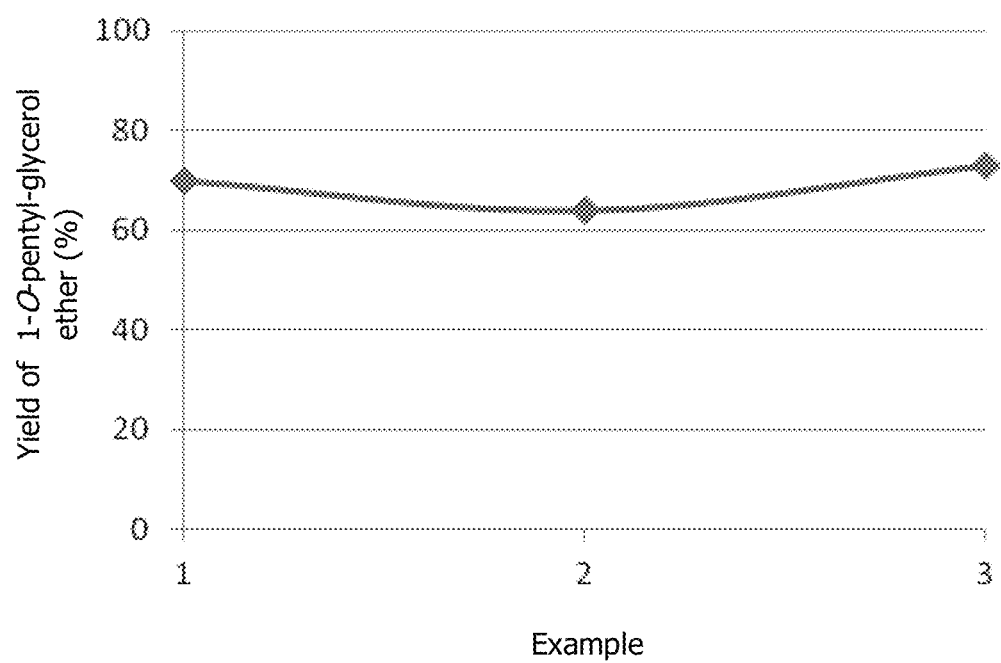

PROCESS FOR PREPARING A POLYOL ETHER

The present invention relates to a process for preparing a polyol ether starting from a polyol and a carboxylic acid or a carboxylic acid ester.

This process makes it possible, inter alia, to carry out the direct, selective synthesis of polyol monoalkyl ethers starting from a polyol and a carboxylic acid or a carboxylic acid ester in mild conditions.

PRIOR ART

The synthesis of symmetric or nonsymmetric ethers is generally carried out according to the Williamson reaction, which is well known by a skilled person in the art as one of the oldest organic reactions used industrially for carrying out this type of transformation. This synthesis route consists of reacting an alcoholate ion, formed by deprotonation of the corresponding alcohol by a base, with a halogenated derivative to form an ether.

However, this reaction has a number of drawbacks, since it requires the use of strong bases such as sodium hydride, sodium hydroxide or potassium hydroxide, making it unsuitable for molecules that are sensitive to bases.

Other alkylation processes involving reaction of very reactive molecules such as aldehydes or ketones with polyols to obtain alkylated polyols in the presence of catalysts and hydrogen have also been described.

International patent application WO 2010/027663 A1 and U.S. Pat. No. 5,446,210, which describe in a general way the synthesis of polyol ethers starting from an aldehyde or a ketone and a polyol via a reductive catalytic alkylation, may be mentioned.

One of the major drawbacks of these alkylation processes is essentially the difficulty of production, the instability and the generally high cost of the starting aldehydes and ketones.

None of these documents describes or suggests a synthesis route and operating conditions for obtaining polyol ethers starting from a carboxylic acid or a carboxylic acid ester.

DESCRIPTION OF THE DRAWINGS

FIG. 1 shows the variation of the yield of 1-O-pentyl-glycerol ether after recycling the catalytic system for examples 30, 31 and 32 (1, 2 and 3 respectively).

DESCRIPTION OF THE INVENTION

The general aim of the present invention is to provide a new route for producing molecules derived from polyols, for instance, alkylated polyols and preferably selectively monoalkylated polyols.

A further aim of the present invention is to propose a novel O-alkylation reaction starting from reagents that are stable and readily available commercially or by synthesis, such as carboxylic acids or carboxylic acid esters.

A further aim of the present invention is to provide a reaction that can be carried out in mild conditions, i.e. compatible, for example, with functional groups that are sensitive to bases, and easily using starting reagents that do not require special handling care (for example, owing to their instability with respect to oxidation) and at a reduced cost using starting reagents that are generally readily accessible.

Thus, according to a first aspect, the present application relates to a process for preparing a polyol ether of formula (I), comprising a step of reductive alkylation involving a compound of general formula (II) and a compound of general formula (III):

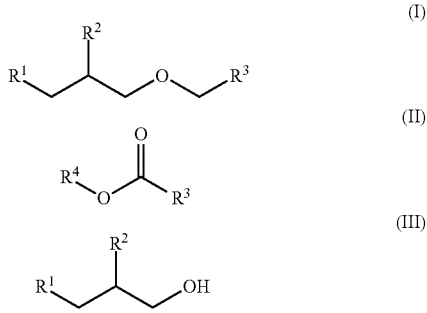

in which:
$R^1$ and $R^2$ are independently selected from the group consisting of hydrogen atom, —OH, —(OCH$_2$—CH(OH)—CH$_2$)$_p$—OH with $1 \leq p \leq 10$, $C_1$-$C_{50}$ alkyl, $C_2$-$C_{50}$ alkenyl, $C_1$-$C_{50}$ alkyl interrupted by one or more oxygen atom(s), $C_2$-$C_{50}$ alkenyl interrupted by one or more oxygen atom(s), aryl, aryloxy, $C_3$-$C_8$ cycloalkyl, and $C_3$-$C_{18}$ cycloalkoxy, wherein said alkyl, alkenyl, aryl, aryloxy, $C_3$-$C_8$ cycloalkyl, $C_3$-$C_{18}$ cycloalkoxy groups may be unsubstituted or substituted;

$R^4$ is selected from the group consisting of a hydrogen atom, $C_1$-$C_{50}$ alkyl, $C_2$-$C_{50}$ alkenyl, aryl, $C_3$-$C_8$ cycloalkyl, and —CH$_2$—CH[O—[C(=O)]$_n$—R$_5$]-CH$_2$—O—[C(=O)]$_m$—R$_6$, wherein said $C_1$-$C_{50}$ alkyl, $C_2$-$C_{50}$ alkenyl, aryl, $C_3$-$C_8$ cycloalkyl, —CH$_2$—CH[O—[C(=O)]$_n$—R$_5$]—CH$_2$—O—[C(=O)]$_m$—R$_6$ may be unsubstituted or substituted;

$R^3$, $R^5$ and $R^6$ are independently selected from the group consisting of $C_1$-$C_{50}$ alkyl, $C_2$-$C_{50}$ alkenyl, aryl, and $C_3$-$C_8$ cycloalkyl, wherein said groups may be unsubstituted or substituted;

n and m are independently equal to 0 or 1;
$R^5$ is a hydrogen atom when n=0;
$R^6$ is a hydrogen atom when m=0;
and wherein at least one of $R^1$ and $R^2$ is a hydroxyl group —OH.

It is important to note that a skilled person in the art would immediately understand that the process according to the invention is intended to apply in general to the reaction of any molecule of general formula (III) provided it possesses a hydroxyl group —OH available for alkylation, as well as to any molecule of general formula (II) provided it can react with a hydroxyl group —OH, available for alkylation, of a molecule of general formula (III).

Therefore the general principle of the present invention is the synthesis of a polyol in which a hydroxyl group —OH, and preferably in which only one hydroxyl group —OH among several other hydroxyl groups —OH, chemically equivalent or not, is alkylated by a functional group derived from a carboxylic acid or from a carboxylic acid ester.

According to an advantageous embodiment, said reductive alkylation step will be carried out in the presence of a catalyst selected from palladium on charcoal, ruthenium tin, Ru/C, Pd/Al$_2$O$_3$, Pd/SiO$_2$, in an amount of less than 5 mol %, preferably in an amount of less than 2 mol %, and more preferably in an amount of less than 1 mol % of catalyst relative to the amount of compound of general formula (II).

It is of course possible to use, in the context of the present invention, any catalyst comprising palladium, rhodium, ruthenium, cobalt, platinum, iridium, nickel or some other metal known to catalyze a hydrogenation reaction, said catalyst optionally being combined with a support selected from charcoal, alumina, silica or aluminosilicate.

According to another advantageous embodiment, this hydrogenation step is carried out at a temperature below 200° C., preferably below 180° C. and even more preferably below 150° C.

According to a particularly advantageous embodiment, this reductive alkylation step is carried out in the presence of an acid catalyst (Brnsted acid or Lewis acid) preferably selected from camphosulfonic acid, paratoluenesulfonic acid, the sulfonic acid resins (AMBERLYST® (a polymer based catalyst), NAFION® (a perfluorinated resin-sulfonic acid catalyst) type), trifluoroacetic acid, silica, silica-alumina, phosphoric acid supported on silica, $BF_3.Et_2O$ or zeolites, advantageously in an amount of less than 10 wt %, preferably less than 5 wt %, relative to the total weight of the compound of general formula (II).

The acid catalysts on a solid support, such as the sulfonic acid resins, are particularly advantageous, in that they can easily be extracted from the reaction mixture after reaction by simple filtration, for optional reuse.

According to another particularly advantageous embodiment, the acid catalyst is an acid catalyst that is on a solid support, forming, with the aforementioned metal catalyst, a recyclable catalytic system.

The catalytic system, metal catalyst/acid catalyst on solid support (for example Pd/C/AMBERLYST® (a polymer based catalyst)), used in the process according to the invention may be recycled, i.e. used several times, namely at least 3 times, or even at least 10 times, or even at least 20 times, without significant loss of yield or of selectivity (in favor of the formation of a polyol of formula (I)). Usually this system will be used between 3 and 10 times.

This, for instance, enables the process of the invention to be compatible with a "continuous" industrial process.

"Significant loss of yield" means a change in yield of at most 50%, of at most 30%, of at most 20%, of at most 10%, of at most 5% and preferably of at most 1% between the yield of the "n-th" reaction (last reaction carried out with the catalytic system) and the highest yield obtained for the preceding reactions from rank 1 (first reaction carried out with the catalytic system) to the rank n–1.

"Significant loss of selectivity" means a change in selectivity of at most 70%, of at most 50%, of at most 30%, of at most 20%, of at most 10%, of at most 5% and preferably of at most 3% between the selectivity of the "n-th" reaction (last reaction carried out with the catalytic system) and the highest selectivity obtained for the preceding reactions from rank 1 (first reaction carried out with the catalytic system) to the rank n–1.

Advantageously, when the compound of general formula (II) is a carboxylic acid, introduction of the acid catalyst can be avoided. In this embodiment the carboxylic acid of general formula (II) can act as acid catalyst of the reaction.

According to another advantageous embodiment, the hydrogenation step is carried out at a pressure of reducing gas, for instance dihydrogen $H_2$, between 1 and 150 bar, preferably between 1 and 100 bar, more preferably between 1 and 50 bar, even more preferably between 10 and 50 bar, and even more preferably between 30 and 50 bar.

An additional advantage of the process according to the invention is that a compound of formula (I) can be obtained in a single reaction step. This provides rapid access to alkylated polyols of more or less complex structures at reduced cost.

The present invention also makes it possible to utilize the world resources of natural polyols such as, for instance, glycerol and derivatives thereof, by using them as raw materials for example in the chemical industry. Such a process can therefore be listed among the so-called "clean" synthesis processes, i.e. contributing to the protection of the environment.

Although, as mentioned above, the process according to the invention has a very general field of application permitting O-alkylation of a polyol starting from a carboxylic acid or from an ester, the aforementioned starting compounds may nevertheless preferably be selected from compounds of formulas (II) and (III) in which:

$R^1$ and $R^2$ are independently selected from the group consisting of hydrogen atom, —OH, —$(OCH_2-CH(OH)-CH_2)_p$—OH with $1 \leq p \leq 10$, $C_1$-$C_{50}$ alkyl, $C_2$-$C_{50}$ alkenyl, $C_1$-$C_{50}$ alkyl interrupted by one or more oxygen atom(s), and $C_2$-$C_{50}$ alkenyl interrupted by one or more oxygen atom(s);

$R^3$ is $C_1$-$C_{50}$ alkyl or $C_2$-$C_{50}$ alkenyl and $R^4$ is hydrogen atom or $C_1$-$C_5$ alkyl;

and wherein at least one of $R^1$ and $R^2$ is a hydroxyl group —OH.

More preferably, in the compounds of the aforementioned formulae (II) and (III):

$R^1$ is selected from the group consisting of hydrogen atom, —OH, and —$(OCH_2-CH(OH)-CH_2)_p$—OH with $1 \leq p \leq 10$;

$R^2$ is a hydroxyl group —OH;

$R^3$ is $C_1$-$C_{28}$ alkyl, preferably $C_1$-$C_{24}$ alkyl or $C_2$-$C_{28}$ alkenyl, preferably $C_2$-$C_{24}$ alkenyl.

Even more preferably, in the aforementioned formula (III), $R^1$ and $R^2$ both represent a hydroxyl group —OH.

Examples of compounds of general formula (III) that may be used in the process according to the invention, are glycerol, glycerol derivatives and other polyhydroxylated substrates such as 1,2-ethanediol, 1,2-propanediol, 1,3-propanediol, 1,4-butanediol, pentaerythritol, trimethylolpropane, polyglycerols, polyoxyethylenes, polyoxypropylenes.

As for the compound of general formula (II), it may be selected more preferably from valeric acid, caproic acid, adipic acid, pelargonic acid, azelaic acid, brassylic acid, myristic acid, stearic acid, oleic acid, 9Z-octadecenoic acid, erucic acid and the corresponding methyl esters.

Without any particular limitation, the compounds of general formula (II) can also be selected from fatty acids, fatty esters or triglycerides or any other natural substances or derivatives of natural substances having at least one carboxylic acid or ester function.

Among these natural substances or derivatives of natural substances we may mention soya oil, sunflower oil, colza oil, linseed oil, olive oil, castor oil, peanut oil, palm oil, etc.

The present invention is of course not limited to the type of equipment for heating, pressurization and/or stirring used in the process.

The process can also be carried out using all types of microwave equipment that can supply the necessary temperature and pressure for carrying out the process according to the invention.

As a general rule a compound of formula (II) and a compound of formula (III) will be used in molar proportions between 1/1 and 1/50 and preferably between 1/2 and 1/10.

The isolated yields are advantageously greater than 10%, preferably greater than 15%, more preferably greater than 20%, preferably between 22% and 71% and more preferably between 22% and 90%.

In the context of the present description, "isolated yield" means the yield by weight calculated from the product of general formula (I) isolated/purified from the crude reaction mixture by one or more method(s) of purification known by a person skilled in the art.

In the context of the present description, "alkyl" means a linear or branched saturated hydrocarbon chain of chemical formula $C_nH_{2n+1}$. As an example of alkyl group, we may mention the groups methyl, ethyl, n-propyl, isopropyl, n-butyl, isobutyl, sec-butyl, t-butyl, pentyl, capryl, lauryl, myristyl, palmityl, stearyl, arachidyl, lignoceryl, etc.

In the context of the present description, "alkenyl" means a linear or branched hydrocarbon chain having at least one unsaturation.

In the context of the present description, "aryl" means a monocyclic or polycyclic group having a delocalized system of π electrons of the type (4n+2) in which n is an integer, including rings only containing carbon atoms, but also rings containing at least one heteroatom selected from N, O and S (i.e. heteroaryl groups).

Examples of aryl groups are, for instance, phenyl, naphthyl, pyrridyl, furyl, furanyl, thienyl, pyrrolyl, indolyl, imidazolyl, thiazolyl, pyrrolidyl, pyrimidyl.

In the context of the present description, "aryloxy" means an aryl group bound to an oxygen atom.

In the context of the present description, "cycloalkyl" means a monocyclic or polycyclic saturated hydrocarbon group, preferably containing from 1 to 3 rings and from 3 to 7 carbon atoms per ring that may also be fused to an unsaturated $C_3$-$C_7$ carbocyclic ring. Examples of such cycloalkyl groups are, for instance, cyclopropyl, cyclobutyl, cyclopentyl, cyclohexyl, cycloheptyl, cyclooctyl, cyclodecyl, cyclododecyl, adamantyl, etc. The term "cycloalkyl" also comprises substituted or unsubstituted cyclic groups containing at least one heteroatom selected from N, O and S (i.e. heterocyclic groups).

In the context of the present description, "cycloalkoxy" means a cycloalkyl group bound to an oxygen atom.

The alkyl, alkenyl, aryl, aryloxy, cycloalkyl and cycloalkoxy groups whose definition has just been mentioned can be substituted with one or more substituents generally selected from the group consisting of halogen atoms, hydroxyl, alkoxy, oxo, alkanoyl, aryloxy, alkanoyloxy, amino, alkylamino, arylamino, aralkylamino, alkanoylamino, aroylamino, aralkanoylamino, thiol, alkylthio, arylthio, aralkylthio, alkylthiono, arylthiono, aralkylthiono, alkylsulfonyl, arylsulfonyl, aralkylsulfonyl, sulfonamido, nitro, cyano, carboxy, carbamyl, alkoxycarbonyl, aryl, guanidino, and heterocyclyl.

In the context of the present description, "O-alkylation" means the formation of a covalent bond between an oxygen atom of a substrate and an alkyl group or a derivative of an alkyl group.

In the context of the present description, "polyol" means an organic compound containing at least two hydroxyl groups —OH such as, for example, (1,n)-diols, glycerols and derivatives thereof.

In the context of the present description, "carboxylic acid" means any organic substance possessing at least one carboxyl function —COOH.

The embodiments and reaction conditions preferred and envisaged in the context of the present invention are, in particular, those corresponding to the combinations, according to the invention, of each of the alternatives from one of the aforementioned lists with each of the alternatives from the other aforementioned lists.

Consequently, each combination of elements from the aforementioned lists of alternatives relating to the choice of:
 the catalyst and of the amount of catalyst,
 the acid catalyst and of the amount of acid catalyst,
 the pressure of dihydrogen $H_2$,
 the reaction temperature,
 the chemical structure and of the amount of compound (II),
 the chemical structure and of the amount of compound (III),
is particularly envisaged in the context of the present invention.

The products obtained by a process according to the invention can be used in various fields of application, for instance, as stimulants for the formation of blood cells in the bone marrow, as anti-inflammatory and antitumor agents, as additive in the preparation of antiperspirant formulations, as additive for formulations intended for skin care, as additive in deodorant formulations, in the formulation of cleaning compositions for body hygiene or else as emulsifiers.

The invention will now be illustrated by the following non limiting examples.

Experiments Carried Out

The acids or esters were purchased from Acros, Sigma-Aldrich. The starting reagents, catalysts, and acid co-catalysts were purchased from Strem, Acros, Sigma-Aldrich. All the reagents were used without additional purification. The measurements of exact mass were carried out with a Thermo DSQ GC/MS equipped with a column of type DB5 (0.15 mm, 40 m), using the following method:

Oven Method
 Initial Temperature (C): 70
 Initial Time (min): 2.00
 Number of Ramps: 1
 Rate #1 (deg/min): 15.0
 Final Temperature #1 (C): 330
 Hold Time #1 (min): 15.00
 Post Run Temperature: Off
 Enable Cryogenics Off
 Maximum Temperature (C): 350
 Prep Run Timeout (min): 10.00
 Equilibration Time (min): 0.50
Right SSL Method
 Base Temperature: On
 Base Temperature (C): 220
 Mode: Split
 Split Flow On
 Split Flow Flow (ml/min): 50
 Splitless Time (min): 1.00
 Surge Pressure Off
 Surge Pressure (kPa): 3.00
 Surge Duration (min): 0.00
 Constant Purge On
 Stop Purge At: (min): 0.00
Right Carrier Method
 Mode: Constant Flow
 Initial Value On
 Initial Value (ml/min): 1.20
 Initial Time: 1.00
 Gas Saver On
 Gas Saver Flow (ml/min): 20
 Gas Saver Time: 5.00
 Vacuum Compensation On

EXAMPLE 1

A stirred autoclave was charged, at room temperature, with 65.60 g (712 mmol) of glycerol, 1.58 g (17.9 mmol) of butyric acid, 0.16 g (10 wt %) of AMBERLYST® (a polymer based catalyst) 35 resin and 0.39 g (1.0 mol %) of Pd/C at 5%. The autoclave was then pressurized at 50 bar of dihydrogen gas $H_2$, and then was heated at 120° C. for 16 h, under vigorous stirring. After 16 h of reaction, the reaction mixture was cooled down to room temperature. The catalyst was filtered through a MILLIPORE® filter (a membrane filter) (0.45 μm) and was rinsed with absolute ethanol. The solvents were evaporated and the organic products were extracted from the glycerol phase using $CH_2Cl_2$ (3×50 ml). The organic phases were combined and then was washed with water (2×30 ml) and $CH_2Cl_2$ was evaporated under reduced pressure. The crude reaction product was purified on a flash silica column (eluent: cyclohexane/ethyl acetate=4:1~1:1). 1-O-butyl-glycerol ether was obtained with an isolated yield of 68%.

EXAMPLE 2

A stirred autoclave was charged, at room temperature, with 68.37 g (742 mmol) of glycerol, 1.80 g (17.6 mmol) of valeric acid, 0.18 g (10 wt %) of AMBERLYST® (a polymer based catalyst) 35 resin and 0.39 g (1.0 mol %) of Pd/C at 5%. The autoclave was then pressurized at 50 bar of dihydrogen gas $H_2$, and then was heated at 120° C. for 16 h, stirring vigorously. After 16 h of reaction, the reaction mixture was brought back to room temperature. The catalyst was filtered on a MILLIPORE® filter (a membrane filter) (0.45 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=4:1~1:1). 1-O-pentyl-glycerol ether was obtained at an isolated yield of 71%.

EXAMPLE 3

A stirred autoclave was charged, at room temperature, with 65.73 g (714 mmol) of glycerol, 1.80 g (17.6 mmol) of valeric acid, 0.18 g (10 wt %) of AMBERLYST® (a polymer based catalyst) 35 resin and 0.39 g (1.0 mol %) of Pd/C at 5%. The autoclave was then pressurized at 50 bar of dihydrogen gas $H_2$, and then it was heated at 120° C. for 16 h, stirring vigorously. After 16 h of reaction, the mixture was brought back to room temperature. The catalyst was filtered on a MILLIPORE® filter (a membrane filter) (0.45 μm) and was rinsed with absolute ethanol. The solvents were evaporated and the organic products were extracted from the glycerol phase by extraction with $CH_2Cl_2$ (3×50 ml). The organic phase was washed with water 2×30 ml) and the $CH_2Cl_2$ was then evaporated at reduced pressure. The crude reaction product was purified on a flash silica column (eluent: cyclohexane/ethyl acetate=4:1~1:1). 1-O-pentyl-glycerol ether was obtained at an isolated yield of 72%.

EXAMPLE 4

A stirred autoclave was charged, at room temperature, with 65.76 g (714 mmol) of glycerol, 2.15 g (17.6 mmol) of methyl valerate, 0.23 g (10 wt %) of camphosulfonic acid and 0.40 g (1.0 mol %) of Pd/C at 5%. The autoclave was then pressurized at 50 bar of dihydrogen gas $H_2$, and then it was heated at 140° C. for 16 h, stirring vigorously. After 16 h of reaction, the reaction mixture was brought back to room temperature. The catalyst was filtered on a MILLIPORE® filter (a membrane filter) (0.45 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=4:1~1:1). 1-O-pentyl-glycerol ether was obtained at an isolated yield of 58%.

EXAMPLE 5

A stirred autoclave was charged, at room temperature, with 55.2 g (600 mmol) of glycerol, 3.9 g (30 mmol) of methyl caproate, 0.39 g (10 wt %) of camphosulfonic acid and 0.3 g (0.5 mol %) of Pd/C at 5%. The autoclave was then pressurized at 10 bar of dihydrogen gas $H_2$, and then it was heated at 140° C. for 24 h, stirring vigorously. After 24 h of reaction, the reaction mixture was brought back to room temperature. The catalyst was filtered on a MILLIPORE® filter (a membrane filter) (0.45 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was analyzed by GC/MS. 1-O-hexyl-glycerol ether was obtained at 22% GC yield.

EXAMPLE 6

A stirred autoclave was charged, at room temperature, with 55.2 g (600 mmol) of glycerol, 3.9 g (30 mmol) of methyl caproate, 0.4 g (10 wt %) of camphosulfonic acid and 0.3 g (0.5 mol %) of Pd/C at 5%. The autoclave was then pressurized at 20 bar of dihydrogen gas $H_2$, and then it was heated at 140° C. for 24 h, stirring vigorously. After 24 h of reaction, the reaction mixture was brought back to room temperature. The catalyst was filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was analyzed by GC/MS. 1-O-hexyl-glycerol ether was obtained at 30% GC yield.

EXAMPLE 7

A stirred autoclave was charged, at room temperature, with 55.2 g (600 mmol) of glycerol, 3.9 g (30 mmol) of methyl caproate, 0.4 g (10 wt %) of camphosulfonic acid and 0.3 g (0.5 mol %) of Pd/C at 5%. The autoclave was then pressurized at 30 bar of dihydrogen gas $H_2$, and then it was heated at 140° C. for 24 h, stirring vigorously. After 24 h of reaction, the reaction mixture was brought back to room temperature. The catalyst was then filtered on a MILLIPORE® filter (a membrane filter)(0.45 μm) and was rinsed with absolute ethanol. The solvents were then evaporated and the organic products were extracted from the glycerol phase by extraction with $CH_2Cl_2$ (3×50 ml). The organic phase was washed with water (2×20 ml) and the $CH_2Cl_2$ was then evaporated at reduced pressure. The crude reaction product was analyzed by GC/MS. 1-O-hexyl-glycerol ether was obtained at 50% GC yield.

EXAMPLE 8

A stirred autoclave was charged, at room temperature, with 55.2 g (600 mmol) of glycerol, 3.9 g (30 mmol) of methyl caproate, 0.4 g (10 wt %) of camphosulfonic acid and 0.3 g (0.5 mol %) of Pd/C at 5%. The autoclave was then pressurized at 40 bar of dihydrogen gas $H_2$, and then it was heated at 140° C. for 24 h, stirring vigorously. After 24 h of reaction, the reaction mixture was brought back to room temperature. The catalyst was then filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (3×50 ml). The organic phase was washed with water (2×20 ml) and the $CH_2Cl_2$ was then evaporated at reduced pressure. The crude reaction product was analyzed by GC/MS. 1-O-hexyl-glycerol ether was obtained at 55% GC yield.

EXAMPLE 9

A stirred autoclave was charged, at room temperature, with 55.2 g (600 mmol) of glycerol, 3.9 g (30 mmol) of methyl caproate, 0.4 g (10 wt %) of camphosulfonic acid and 0.6 g (1 mol %) of Pd/C at 5%. The autoclave was then pressurized at 50 bar of dihydrogen gas $H_2$, and then it was heated at 140° C. for 24 h, stirring vigorously. After 24 h of reaction, the reaction mixture was brought back to room temperature. The catalyst was then filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (3×50 ml). The organic phase was washed with water (2×20 ml) and the $CH_2Cl_2$ was then evaporated at reduced pressure. The crude reaction product was analyzed by GC/MS. 1-O-hexyl-glycerol ether was obtained at 58% GC yield.

EXAMPLE 10

A stirred autoclave was charged, at room temperature, with 66.75 g (725 mmol) of glycerol, 2.05 g (17.6 mmol) of caproic acid, 0.20 g (10 wt %) of AMBERLYST® (a polymer based catalyst) 35 resin and 0.39 g (1.0 mol %) of Pd/C at 5%. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was then filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (3×50 ml). The organic phase was washed with water (2×20 ml) and the $CH_2Cl_2$ was then evaporated at reduced pressure. The crude reaction product was purified on a flash silica column (eluent: cyclohexane/ethyl acetate=4:1~1:1). 1-O-hexyl-glycerol ether was obtained at an isolated yield of 70%.

EXAMPLE 11

A stirred autoclave was charged, at room temperature, with 65.50 g (711 mmol) of glycerol, 2.29 g (17.6 mmol) of methyl caproate, 0.23 g (10 wt %) of camphosulfonic acid and 0.39 g (1 mol %) of Pd/C at 5%. The autoclave was then pressurized at 50 bar of dihydrogen gas $H_2$, and then it was heated at 140° C. for 16 h, stirring vigorously. After 16 h of reaction, the reaction mixture was brought back to room temperature. The catalyst was then filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (3×50 ml). The organic phase was washed with water (2×20 ml) and the $CH_2Cl_2$ was then evaporated at reduced pressure. The crude reaction product was analyzed by GC/MS. 1-O-hexyl-glycerol ether was obtained at 83% GC yield.

EXAMPLE 12

A stirred autoclave was charged, at room temperature, with 65.84 g (715 mmol) of glycerol, 2.29 g (17.6 mmol) of methyl caproate, 0.23 g (10 wt %) of camphosulfonic acid and 0.39 g (1 mol %) of Pd/C at 5%. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was then filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (3×50 ml). The organic phase was washed with water (2×20 ml) and the $CH_2Cl_2$ was then evaporated at reduced pressure. The crude reaction product was analyzed by GC/MS. 1-O-hexyl-glycerol ether was obtained at 59% GC yield.

EXAMPLE 13

A stirred autoclave was charged, at room temperature, with 65.61 g (712 mmol) of glycerol, 2.29 g (17.6 mmol) of methyl caproate, 0.23 g (10 wt %) of AMBERLYST® (a polymer based catalyst) 15 resin and 0.23 g (1 mol %) of Pd/C at 5%. The autoclave was then pressurized at 50 bar of dihydrogen gas $H_2$, and then it was heated at 140° C. for 16 h, stirring vigorously. After 16 h of reaction, the reaction mixture was brought back to room temperature. The catalyst was then filtered on a MILLIPORE® filter (a membrane filter) (0.45 pm) and was rinsed with absolute ethanol. The solvents were then evaporated and the organic products were extracted from the glycerol phase by extraction with $CH_2Cl_2$ (3×50 ml). The organic phase was washed with water (2×20 ml) and the $CH_2Cl_2$ was then evaporated at reduced pressure. The crude reaction product was analyzed by GC/MS. 1-O-hexyl-glycerol ether was obtained at 62% GC yield.

EXAMPLE 14

A stirred autoclave was charged, at room temperature, with 66.47 g (722 mmol) of glycerol, 2.53 g (17.5 mmol) of octanoic acid, 0.25 g (10 wt %) of camphosulfonic acid and 0.39 g (1.0 mol %) of Pd/C at 5%. The autoclave was then pressurized at 50 bar of dihydrogen gas $H_2$, and then it was heated at 140° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=4:1~1:1). 1-O-octanyl-glycerol ether was obtained at an isolated yield of 52%.

EXAMPLE 15

A stirred autoclave was charged, at room temperature, with 65.63 g (713 mmol) of glycerol, 2.54 g (17.6 mmol) of octanoic acid, 0.26 g (10 wt %) of AMBERLYST® (a polymer based catalyst) 35 resin and 0.39 g (1.0 mol %) of Pd/C at 5%. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent:cyclohexane/ethyl acetate=4:1~1:1). 1-O-octanyl-glycerol ether was obtained at an isolated yield of 48%.

EXAMPLE 16

A stirred autoclave was charged, at room temperature, with 69 g (750 mmol) of glycerol, 3.9 g (25 mmol) of pelargonic acid, 0.39 g (10 wt %) of camphosulfonic acid and 0.63 g (1 mol %) of Pd/C at 5%. The autoclave was then pressurized at 40 bar of dihydrogen gas $H_2$, and then it was heated at 140° C. for 24 h, stirring vigorously. After 24 h of reaction, the reaction mixture was brought back to room temperature. The catalyst was then filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (3×100 ml). The organic phase was washed with water (2×30 ml) and the $CH_2Cl_2$ was then evaporated at reduced pressure. The crude reaction product was analyzed by GC/MS and 1-O-nonyl glycerol ether was obtained at a GC yield of 43%.

EXAMPLE 17

A stirred autoclave was charged, at room temperature, with 55.2 g (600 mmol) of glycerol, 51.6 g (30 mmol) of methyl pelargonate, 0.039 g (10 wt %) of camphosulfonic acid and 0.64 g (1 mol %) of Pd/C at 5%. The autoclave was then pressurized at 10 bar of dihydrogen gas $H_2$, and then it was heated at 145° C. for 24 h, stirring vigorously. After 24 h of reaction, the reaction mixture was brought back to room temperature. The catalyst was then filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (3×50 ml). The organic phase was washed with water (2×20 ml) and the $CH_2Cl_2$ was then evaporated at reduced pressure. 1-O-nonyl-glycerol ether was obtained by purification on a flash silica column with ethyl acetate/cyclohexane mixture 1/4 to 1/1 as eluent with an isolated yield of 20%.

EXAMPLE 18

A stirred autoclave was charged, at room temperature, with 65.35 g (710 mmol) of glycerol, 3.01 g (17.5 mmol) of decanoic acid, 0.30 g (10 wt %) of AMBERLYST® (a polymer based catalyst) 35 resin and 0.39 g (1.0 mol %) of Pd/C at 5%. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent:cyclohexane/ethyl acetate=4:1~1:1). 1-O-decanyl-glycerol ether was obtained at an isolated yield of 46%.

EXAMPLE 19

A stirred autoclave was charged, at room temperature, with 65.43 g (711 mmol) of glycerol, 3.50 g (17.5 mmol) of dodecanoic acid, 0.35 g (10 wt %) of AMBERLYST® (a polymer based catalyst) 35 resin and 0.39 g (1.0 mol %) of Pd/C at 5%. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=5:1~1:1). 1-O-dodecanyl-glycerol ether was obtained at an isolated yield of 42%.

EXAMPLE 20

A stirred autoclave was charged, at room temperature, with 67 g (728 mmol) of glycerol, 8.2 g (36 mmol) of methyl tridecylate, 0.82 g (10 wt %) of camphosulfonic acid and 0.74 g (1.0 mol %) of Pd/C at 5%. The autoclave was then pressurized at 50 bar of dihydrogen gas $H_2$, and then it was heated at 140° C. for 24 h, stirring vigorously. After 24 h of reaction, the reaction mixture was brought back to room temperature. The catalyst was then filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (3×50 ml). The organic phase was washed with water (2×20 ml) and the $CH_2Cl_2$ was then evaporated at reduced pressure. The crude reaction product was analyzed by GC/MS. 1-O-tridecyl-glycerol ether was obtained at 16% GC yield.

EXAMPLE 21

A stirred autoclave was charged, at room temperature, with 67 g (728 mmol) of glycerol, 8.2 g (36 mmol) of myristic acid, 0.21 g (5 wt %) of camphosulfonic acid and 0.74 g (1 mol %) of Pd/C at 5%. The autoclave was then pressurized at 40 bar of dihydrogen gas $H_2$, and then it was heated at 140° C. for 24 h, stirring vigorously. After 24 h of reaction, the reaction mixture was brought back to room temperature. The catalyst was then filtered on MILLIPORE® filter (a membrane filter) (0.45 μm) and was rinsed with absolute ethanol. The solvents were then evaporated and the organic products were extracted from the glycerol phase by extraction with $CH_2Cl_2$ (3×100 ml). The organic phase was washed with water (2×30 ml) and the $CH_2Cl_2$ was then evaporated at reduced pressure. The crude reaction product was analyzed by GC/MS and 1-O-tetradecyl glycerol ether was obtained at a GC yield of 71% and, after purification on a flash silica column with ethyl acetate/cyclohexane 1/4 to 1/1 as eluent, it was obtained at an isolated yield of 36%.

EXAMPLE 22

A stirred autoclave was charged, at room temperature, with 65.41 g (710 mmol) of glycerol, 4.01 g (17.6 mmol) of myristic acid, 0.40 g (10 wt %) of AMBERLYST® (a polymer based catalyst) 35 resin and 0.39 g (1.0 mol %) of Pd/C at 5%. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=5:1~1:1). 1-O-tetradecanyl-glycerol ether was obtained at an isolated yield of 41%.

EXAMPLE 23

A stirred autoclave was charged, at room temperature, with 69.14 g (751 mmol) of glycerol, 12.34 g (61.6 mmol) of palmitic acid, 1.29 g (10 wt %) of camphosulfonic acid and 1.39 g (1.0 mol %) of Pd/C at 5%. The autoclave was then pressurized at 50 bar of dihydrogen gas $H_2$, and then it was heated at 140° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=6:1~1:1). 1-O-hexadecanyl-glycerol ether was obtained at an isolated yield of 28%.

EXAMPLE 24

A stirred autoclave was charged, at room temperature, with 68.13 g (740 mmol) of glycerol, 4.40 g (17.2 mmol) of palmitic acid, 0.45 g (10 wt %) of AMBERLYST® (a polymer based catalyst) 35 resin and 0.39 g (1.0 mol %) of Pd/C at 5%. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was filtered on a MILLIPORE® filter (a membrane filter (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=6:1~1:1). 1-O-hexadecanyl-glycerol ether was obtained at an isolated yield of 22%.

EXAMPLE 25

A stirred autoclave was charged, at room temperature, with 92 g (1 mol) of glycerol, 7.1 g (25 mmol) of stearic acid, 0.71 g (10 wt %) of camphosulfonic acid and 0.53 g (1 mol %) of Pd/C at 5%. The autoclave was then pressurized at 50 bar of dihydrogen gas $H_2$, and then it was heated at 140° C. for 24 h, stirring vigorously. After 24 h of reaction, the reaction mixture was brought back to room temperature. The catalyst was then filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (3×100 ml). The organic phase was washed with water (2×30 ml) and the $CH_2Cl_2$ was then evaporated at reduced pressure. 1-O-octadecyl glycerol ether was obtained by purification on a flash silica column with ethyl acetate/cyclohexane 1/4 to 1/1 as eluent, at an isolated yield of 30%.

EXAMPLE 26

A stirred autoclave was charged, at room temperature, with 122.9 g (1.33 mol) of glycerol, 12.5 g (66.5 mmol) of azelaic acid, 1.25 g (10 wt %) of camphosulfonic acid and 3.0 g (2 mol %) of Pd/C at 5%. The autoclave was then pressurized at 60 bar of dihydrogen gas $H_2$, and then it was heated at 140° C. for 24 h, stirring vigorously. After 24 h of reaction, the reaction mixture was brought back to room temperature. The catalyst was then filtered on a MILLIPORE® filter (a membrane filter) (0.45 μm) and was rinsed with absolute ethanol. The solvents were then evaporated and the organic products were extracted from the glycerol phase by extraction with $CH_2Cl_2$ (4×200 ml). The $CH_2Cl_2$ was then evaporated at reduced pressure. The crude reaction product was analyzed by GC/MS. 1,9-O,O-nonyl-glycerol diether was obtained at 30% GC yield.

EXAMPLE 27

A stirred autoclave was charged, at room temperature, with 101.7 g (1.11 mol) of glycerol, 6.55 g (21 mmol) of diacid D18:1, 0.65 g (10 wt %) of camphosulfonic acid and 0.8 g (1.8 mol %) of Pd/C at 5%. The autoclave was then pressurized at 50 bar of dihydrogen gas $H_2$, and then it was heated at 140° C. for 26 h, stirring vigorously. After 26 h of reaction, the reaction mixture was brought back to room temperature. The catalyst was then filtered on a MILLIPORE® filter (a membrane filter) (0.45 μm) and was rinsed with a mixture of $CH_2Cl_2$ and absolute ethanol. The solvents were then evaporated and the organic products were extracted from the glycerol phase by extraction with $CH_2Cl_2$ (3×300 ml). The $CH_2Cl_2$ was then evaporated at reduced pressure. The crude reaction product was analyzed by GC/MS. 1,18-O,O-octadecyl-glycerol diether was obtained at 10% GC yield.

EXAMPLE 28

A stirred autoclave was charged, at room temperature, with 65.66 g (395 mmol) of diglycerol, 1.34 g (11.5 mmol) of caproic acid, 0.13 g (10 wt %) of AMBERLYST® (a polymer based catalyst) 35 resin and 0.26 g (1.0 mol %) of Pd/C at 5%. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ ethyl acetate=2:1~ethyl acetate 100%). 1-O-hexyl-diglycerol ether was obtained at an isolated yield of 57%.

EXAMPLE 29

A stirred autoclave was charged,. at room temperature, with 65.35 g (393 mmol) of diglycerol, 2.26 g (13.1 mmol) of decanoic acid, 0.23 g (10 wt %) of AMBERLYST® (a polymer based catalyst) 35 resin and 0.28 g (1.0 mol %) of Pd/C at 5%. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=2:1~1:1). 1-O-decanyl-diglycerol ether was obtained at an isolated yield of 37%.

Examples 30, 31 and 32

Recycling of the Catalytic System

EXAMPLE 30

A stirred autoclave was charged, at room temperature, with 65.85 g (715 mmol) of glycerol, 1.80 g (17.6 mmol) of valeric acid, 0.18 g (10 wt %) of AMBERLYST® (a polymer based catalyst) 35 resin and 0.39 g (1.0 mol %) of Pd/C at 5%. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=4:1~1:1). 1-O-pentyl-glycerol ether was obtained at an isolated yield of 69%. After the reaction, the mixture of catalysts (AMBERLYST® (a polymer based catalyst) 35 resin and Pd/C) was immersed in 5 ml of methanol, and then transferred to the autoclave. The latter was dried under an argon stream for 4 h at room temperature. After complete evaporation of the solvent, the substrates (glycerol and valeric acid) were added for a fresh reaction (cf. example 31).

EXAMPLE 31

A stirred autoclave was charged, at room temperature, with the mixture of catalysts recycled from example 30 (AMBERLYST® (a polymer based catalyst) 35 and Pd/C), with 66.86 g (726 mmol) of glycerol and 1.80 g (17.6 mmol) of valeric acid. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=4:1~1:1). 1-O-pentyl-glycerol ether was obtained at an isolated yield of 63%.

After the reaction, the mixture of catalysts (AMBERLYST® (a polymer based catalyst) 35 resin and Pd/C) was immersed in 5 ml of methanol, and then transferred to the autoclave. The latter was dried under an argon stream for 4 h at room temperature.

After complete evaporation of the solvents, the substrates (glycerol and valeric acid) were added for a fresh reaction (cf. example 32).

EXAMPLE 32

A stirred autoclave was charged, at room temperature, with the mixture of catalysts recycled from example 31 (AMBERLYST® (a polymer based catalyst) 35 and Pd/C), with 65.56 g (712 mmol) of glycerol and 1.80 g (17.6 mmol) of valeric acid. The autoclave was then pressurized at 50 bar of dihydrogen gas $H_2$, and then it was heated at 120° C. for 16 h, stirring vigorously. After 16 h of reaction, the reaction mixture was brought back to room temperature. The catalyst was filtered on a MILLIPORE® filter (a membrane filter) (0.1 μm) and was rinsed with absolute ethanol. The solvents were evaporated and the organic products were extracted from the glycerol phase by extraction with $CH_2Cl_2$ (3×50 ml). The organic phase was washed with water (2×30 ml) and the $CH_2Cl_2$ was then evaporated at reduced pressure. The crude reaction product was purified on a flash silica column (eluent: cyclohexane/ethyl acetate=4:1~1:1). 1-O-pentyl-glycerol ether was obtained at an isolated yield of 72%.

The catalysts were recycled three times without loss of activity, yield, or selectivity.

The invention claimed is:
1. A process for preparing a polyol ether of formula (I), comprising a step of performing reductive alkylation by contacting a compound of formula (II) with a compound of formula (III):

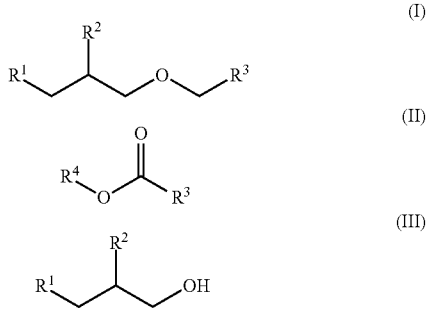

in which:
R$^1$ and R$^2$ are independently selected from the group consisting of hydrogen, —OH, —(OCH$_2$—CH(OH)—CH$_2$)$_p$—OH having p in a range: 1≤p≤10, C$_1$-C$_{50}$ alkyl, C$_2$-C$_{50}$ alkenyl, C$_1$-C$_{50}$ alkyl interrupted by one or more oxygen atom(s), C$_2$-C$_{50}$ alkenyl interrupted by one or more oxygen atom(s), aryl, aryloxy, C$_3$-C$_8$ cycloalkyl, and C$_3$-C$_{18}$ cycloalkoxy group, wherein the alkyl, the alkenyl, the aryl, the aryloxy, the $C_3$-$C_8$ cycloalkyl, the $C_3$-$C_{18}$ cycloalkoxy may be unsubstituted or substituted;

$R^4$ is selected from the group consisting of hydrogen, $C_1$-$C_{50}$ alkyl, $C_2$-$C_{50}$ alkenyl, aryl, $C_3$-$C_8$ cycloalkyl, and —$CH_2$—$CH[O$—$[C(=O)]_n$—$R_5]$—$CH_2$—$O$—$[C(=O)]_m$—$R_6$, wherein the $C_1$-$C_{50}$ alkyl, the $C_2$-$C_{50}$ the alkenyl, the aryl, the $C_3$-$C_8$ cycloalkyl, and the —$CH_2$—$CH[O$—$[C(=O)]_n$—$R_5]$—$CH_2$—$O$—$[C(=O)]_m$—$R_6$ may be unsubstituted or substituted;

$R^3$, $R^5$ and $R^6$ are independently selected from the group consisting of $C_1$-$C_{50}$ alkyl, $C_2$-$C_{50}$ alkenyl, aryl, and $C_3$-$C_8$ cycloalkyl, wherein the $C_1$-$C_{50}$ alkyl, the $C_2$-$C_{50}$ alkenyl, the aryl, and the $C_3$-$C_8$ cycloalkyl may be unsubstituted or substituted;

n and m are independently equal to 0 or 1;

$R^5$ is hydrogen when n=0; and $R^6$ is hydrogen when m=0, wherein at least one of $R^1$ and $R^2$ is a hydroxyl group —OH.

2. The process as claimed in claim 1, wherein said reductive alkylation step is carried out in the presence of a catalyst selected from the group consisting of palladium, rhodium, ruthenium, cobalt, platinum, iridium, and nickel, said catalyst optionally being combined with a support member selected from the group consisting of charcoal, alumina, silica, and aluminosilicate.

3. The process as claimed in claim 2, wherein said catalyst is used in a molar amount of less than 1% relative to a molar amount of the compound of the formula (II).

4. The process as claimed in, claim 1, wherein said reductive alkylation step is carried out at a temperature of lower than 200°C.

5. The process as claimed in claim 1, comprising a single reaction step.

6. The process as claimed in claim 1, wherein said reductive alkylation step is carried out in the presence of an acid catalyst.

7. The process as claimed in claim 6, wherein said acid catalyst is selected from the group consisting of Lewis acids and Brnsted acids.

8. The process as claimed in claim 7, wherein said acid catalyst is selected from the group consisting of camphosulfonic acid, paratoluenesulfonic acid, sulfonic acid resins, trifluoroacetic acid, silica, silica-alumina, phosphoric acid supported on silica, $BF_3.Et_2O$ and zeolites.

9. The process as claimed in claim 6, wherein said acid catalyst is present in an amount of less than 10 wt %, relative to a total weight of the compound of the formula (II).

10. The process as claimed in claim 6, wherein said acid catalyst is an acid catalyst on a solid support member, forming, a recyclable catalytic system with another catalyst selected from the group consisting of palladium, rhodium, ruthenium, cobalt, platinum, iridium, and nickel, which optionally is combined with a support member selected from the group consisting of charcoal, alumina, silica, and aluminosilicate.

11. The process as claimed in claim 6, wherein said acid catalyst is a sulfonic acid resin and is combined with a solid support member.

12. The process as claimed in claim 1, wherein in the aforementioned formulae (I), (II) and (III):

$R^1$ and $R^2$ are independently selected from the group consisting of hydrogen, —OH, —$(OCH_2$—$CH(OH)$—$CH_2)_n$—OH having p in a range: $1 \leq p \leq 10$, $C_1$-$C_{50}$ alkyl, $C_2$-$C_{50}$ alkenyl, $C_1$-$C_{50}$ alkyl interrupted by one or more oxygen atom(s), and $C_2$-$C_{50}$ alkenyl interrupted by one or more oxygen atom(s);

$R^3$ is $C_1$-$C_{50}$ alkyl or $C_2$-$C_{50}$ alkenyl; and $R^4$ is hydrogen or $C_1$-$C_5$ alkyl, wherein at least one of $R^1$ and $R^2$ is the hydroxyl group —OH.

13. The process as claimed in claim 1, wherein in the aforementioned formulae (I) and (III):

$R^1$ is selected from the group consisting of hydrogen, —OH, and —$(OCH_2$—$CH(OH)$—$CH_2)_p$—OH having p in a range: $1 \leq p \leq 10$; and $R^2$ is the hydroxyl group —OH.

14. The process as claimed in claim 1, wherein in the aforementioned formulae (I) and (II):

$R^3$ is $C_1$-$C_{28}$ alkyl or $C_2$-$C_{28}$ alkenyl.

15. The process as claimed in claim 1, wherein in the aforementioned formulae (I) and (III), $R^1$ and $R^2$ each represent the —OH group.

16. The process as claimed in claim 1, wherein said compound of the formula (II) is selected from the group consisting of valeric acid, caproic acid, adipic acid, pelargonic acid, azelaic acid, brassylic acid, myristic acid, stearic acid, oleic acid, 9Z-octadecenoic acid, erucic acid, and corresponding methyl esters thereof.

17. The process as claimed in claim 2, wherein said reductive alkylation step is carried out at a temperature of lower than 200° C.

18. The process as claimed in claim 1, wherein said reductive alkylation step is carried out at a temperature of lower than 150° C.

19. The process as claimed in claim 2, wherein said reductive alkylation step is carried out in the presence of an acid catalyst.

20. The process as claimed in claim 3, wherein said reductive alkylation step is carried out in the presence of an acid catalyst.

21. The process as claimed in claim 4, wherein said reductive alkylation step is carried out in the presence of an acid catalyst.

22. The process as claimed in claim 18, wherein in the aforementioned formulae (I), (II) and (III):

$R^1$ and $R^2$ are independently selected from the group consisting of hydrogen, —OH, —$(OCH_2$—$CH(OH)$—$CH_2)_p$—OH having p in a range: $1 \leq p \leq 10$, $C_1$-$C_{50}$ alkyl, $C_2$-$C_{50}$ alkenyl, $C_1$-$C_{50}$ alkyl interrupted by one or more oxygen atom(s), and $C_2$-$C_{50}$ alkenyl interrupted by one or more oxygen atom(s);

$R^3$ is $C_1$-$C_{50}$ alkyl or $C_2$-$C_{50}$ alkenyl; and $R^4$ is hydrogen or $C_1$-$C_5$ alkyl, wherein at least one of $R^1$ and $R^2$ is the hydroxyl group —OH.

23. The process as claimed in claim 18, wherein in the aforementioned formulae (I) and (III):

$R^1$ is selected from the group consisting of hydrogen, —OH, and —$(OCH_2$—$CH(OH)$—$CH_2)_p$—OH having p in a range: $1 \leq p \leq 10$; and $R^2$ is the hydroxyl group —OH.

24. The process as claimed in claim 10, wherein in the aforementioned formulae (I) and (III):

$R^1$ is selected from the group consisting of hydrogen, —OH, and —$(OCH_2$—$CH(OH)$—$CH_2)_p$—OH having p in a range: $1 \leq p \leq 10$; and $R^2$ is the hydroxyl group —OH.

* * * * *